United States Patent [19]
Picha et al.

[11] Patent Number: 5,951,467
[45] Date of Patent: Sep. 14, 1999

[54] RECONFIGURABLE AND SELF-RETAINING SURGICAL RETRACTOR

[75] Inventors: George J. Picha, Independence; Gary Austin, Euclid; J. Timothy Austin, Concord, all of Ohio

[73] Assignee: Applied Medical Technology, Inc., Cleveland, Ohio

[21] Appl. No.: 09/275,137

[22] Filed: Mar. 23, 1999

[51] Int. Cl.⁶ .................................................. A61B 17/02
[52] U.S. Cl. ........................................... 600/233; 600/206
[58] Field of Search ................................... 600/206, 208, 600/217, 231, 233, 232

[56] References Cited

U.S. PATENT DOCUMENTS

| | | |
|---|---|---|
| Re. 32,021 | 11/1985 | Scott, Jr. . |
| 1,400,616 | 12/1921 | McCrory . |
| 2,384,304 | 9/1945 | helfrick . |
| 2,473,266 | 6/1949 | Wexler . |
| 2,701,562 | 2/1955 | Michael et al. . |
| 2,751,902 | 6/1956 | Lorffler ................................. 600/233 |
| 2,845,925 | 8/1958 | Jayle . |
| 3,168,093 | 2/1965 | Gauthier . |
| 3,203,099 | 8/1965 | Interlandi . |
| 3,509,873 | 5/1970 | Karlin et al. . |
| 3,515,129 | 6/1970 | Truhan . |
| 3,522,790 | 8/1970 | Gautner ................................. 600/233 |
| 3,542,015 | 11/1970 | Steinman . |
| 3,762,401 | 10/1973 | Tupper . |
| 3,823,709 | 7/1974 | McGuire . |
| 3,857,386 | 12/1974 | Ashbell . |
| 3,916,879 | 11/1975 | Cotten . |
| 3,970,075 | 7/1976 | Sindelar et al. . |
| 4,239,036 | 12/1980 | Krieger ................................. 600/206 |
| 4,254,763 | 3/1981 | McCready et al. . |
| 4,337,762 | 7/1982 | Gauthier . |
| 4,355,631 | 10/1982 | LeVahn . |
| 4,421,107 | 12/1983 | Estes et al. . |
| 4,421,108 | 12/1983 | Cabrera et al. ....................... 600/233 |
| 4,430,991 | 2/1984 | Darnell . |
| 4,434,791 | 3/1984 | Darnell . |
| 5,529,358 | 6/1996 | Dinkler et al. ....................... 600/233 |
| 5,582,577 | 12/1996 | Lund et al. .......................... 600/233 |
| 5,769,783 | 6/1998 | Fowler . |
| 5,785,649 | 7/1998 | Fowler, Jr. . |

FOREIGN PATENT DOCUMENTS

| | | |
|---|---|---|
| 1 222 141 | 2/1971 | United Kingdom . |
| 1 550 254 | 8/1979 | United Kingdom . |
| 1 550 255 | 8/1979 | United Kingdom . |

*Primary Examiner*—Paul J. Hirsch
*Attorney, Agent, or Firm*—Pearne, Gordon, McCoy & Granger LLP

[57] ABSTRACT

A surgical retractor frame that is easily reconfigurable and self-maintaining in a desired position. The surgical retractor frame is formed from first and second rigid frame portions that are easily adjusted to various desired configurations. The first and second portions cooperate to define a support adapted to surround a surgical field and operable to releasably receive a plurality of surgical stays for temporary retraction of tissue during a surgical procedure. A malleable connector secures the first frame portion to the second frame portion, and permits the frame portions to be moved relative to one another to permit adjustment and proper positioning of the frame relative to the surgical field. The connector is a preferably a plastic coated wire that is adhesively affixed to the first and second frame portions.

16 Claims, 4 Drawing Sheets

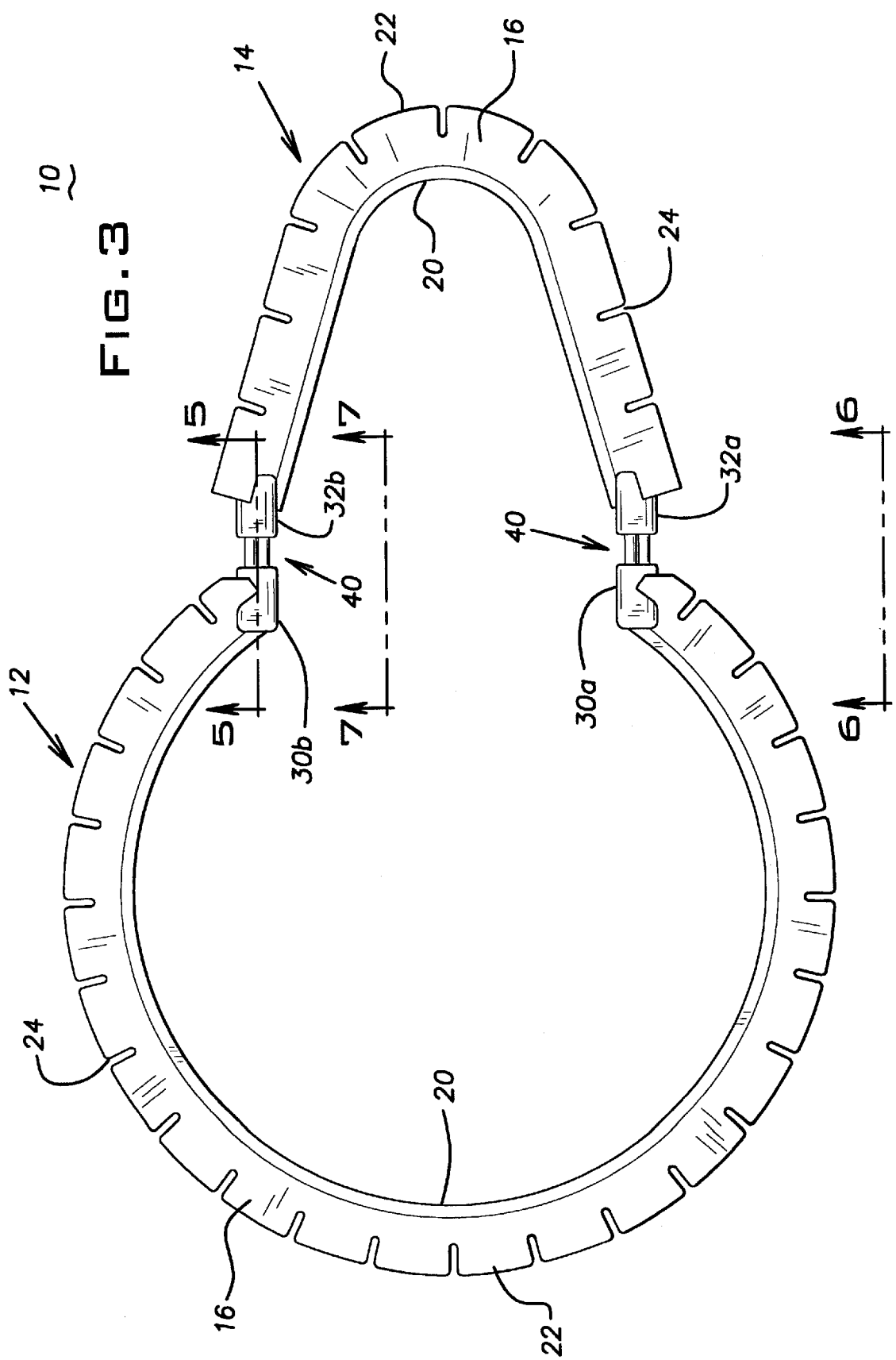

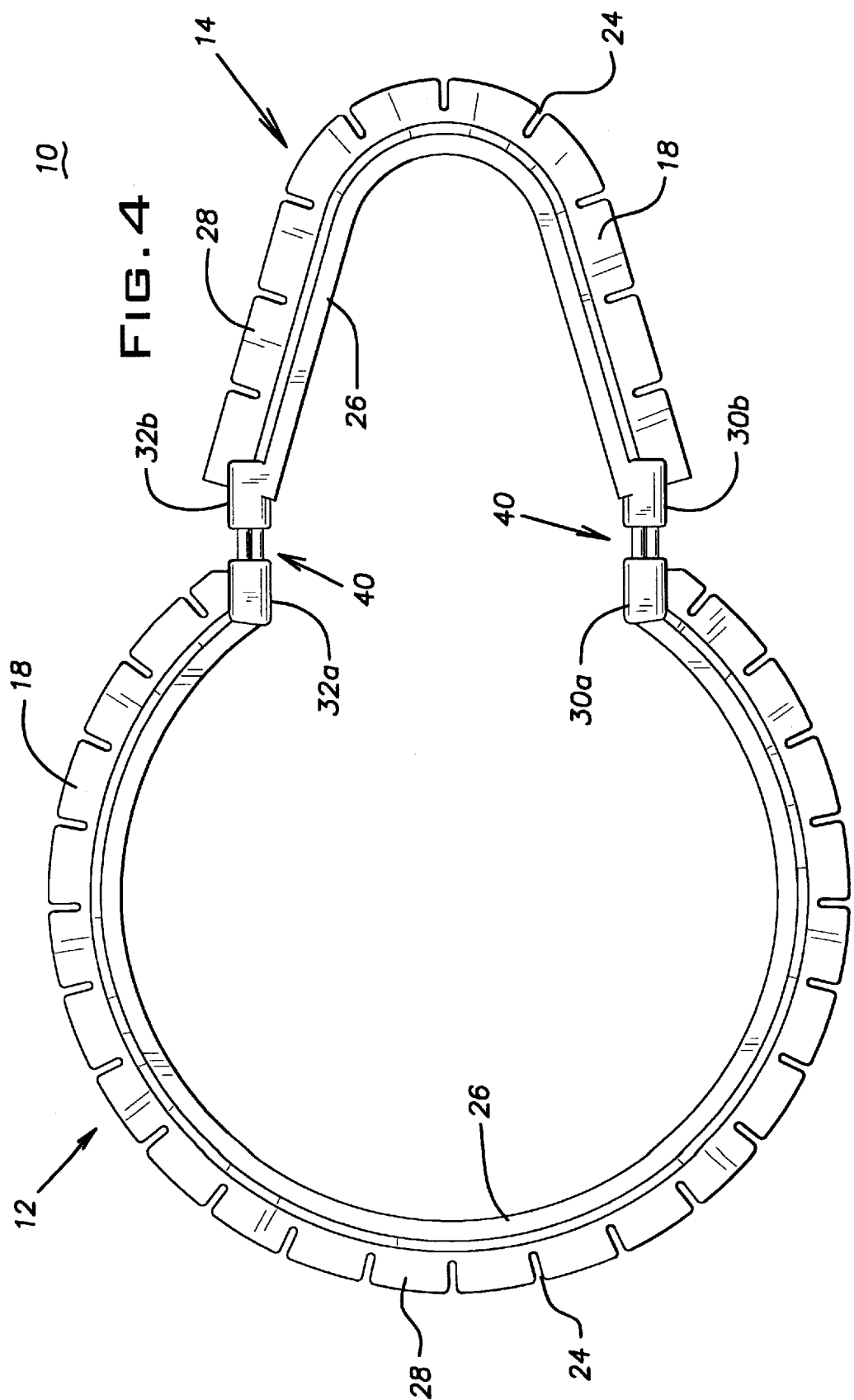

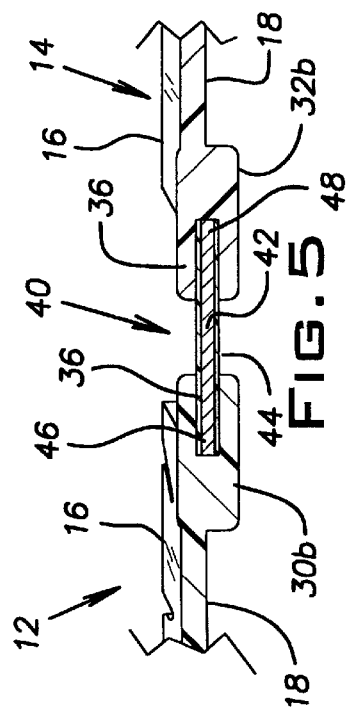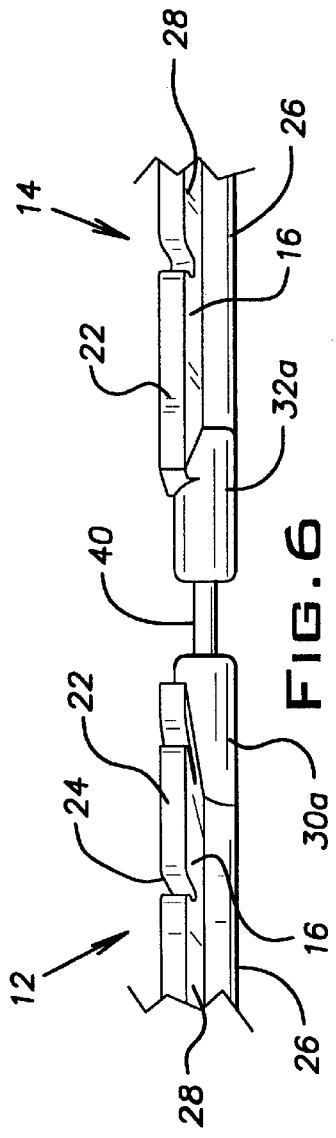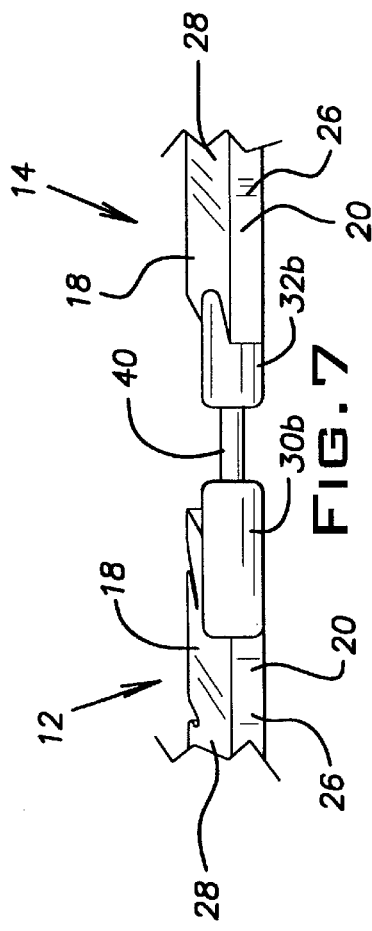

RECONFIGURABLE AND SELF-RETAINING SURGICAL RETRACTOR

BACKGROUND OF THE INVENTION

1. Field of the Invention

The present invention is directed toward surgical retractor systems and, more specifically, to a reconfigurable, self-retaining surgical retractor system.

2. Description of Related Art

It has proven to be desirable in many surgical procedures to provide means to maintain the surgical incision in an open or exposed condition. Several tissue retraction systems have been developed over the years in response to the need for a means to maintain tissue in out of the way of the surgeon. Typically, such systems include a frame or support portion and a tissue-engaging portion.

The frame is typically a rigid, one-piece construction, and often is contoured or designed to fit a specific portion of the human body. As such, conventional frames are not adapted for reconfiguration to different shapes. Surgical frames of this type are illustrated by U.S. Pat. Nos. 5,785,649; 5,769,783; 4,430,991; 3,070,088; and 2,701,562, the disclosures of which are expressly incorporated herein in their entireties.

Other surgical frames have portions that are movable relative to one another. See, for example, U.S. Pat. No. Re. 32,021 and U.S. Pat. No. 4,434,791, the disclosures of which are expressly incorporated herein in their entireties. Each of these frames has a first portion and a second portion that are in engagement with each other and pivotally secured to one another by means of a pair of pivot joints. Unfortunately, the pivotal connection is not easily adjusted, and is an inconvenient means to alter the orientation of the frame portions relative to each other.

Therefore, there exists a need in the art for a surgical frame that is easily reconfigurable and that will retain its shape once reconfigured. There further exists a need in the art for a surgical frame that is rigid and stable while being easily adjusted to the infinite configurations that may be encountered in various surgical applications.

SUMMARY OF THE INVENTION

The present invention is directed toward a surgical retractor frame that is easily reconfigurable and self-maintaining in a desired position. The present invention is further directed toward a surgical frame formed from first and second rigid frame portions that are easily adjusted to various desired configurations.

In accordance with the present invention, a retractor frame is formed from a substantially rigid material, and has a first portion and a second portion. The first and second portions cooperate to define a support adapted to surround a surgical field and operable to releasably receive a plurality of surgical stays for temporary retraction of tissue during a surgical procedure.

In further accordance with the present invention, means are provided for permanently securing the first portion of the frame to the second portion of the frame. The securing means is readily deformable to permit the first and second frame portions to be moved relative to one another to permit adjustment and proper positioning of the frame relative to the surgical field. The securing means is malleable such that deformation thereof may be reversed.

In further accordance with the present invention, the securing means includes a connector that extends between, and is connected to, the first and second frame portions. The connector is a plastic coated wire that is affixed, preferably by adhesives, to the first and second frame portions. In accordance with an alternative construction, the plastic coated wire is molded into the first and second frame portions.

BRIEF DESCRIPTION OF THE DRAWINGS

These and further features of the present invention will be apparent with reference to the drawings, wherein:

FIG. 3 is a top plan view of the surgical frame shown in FIGS. 1 and 2;

FIG. 4 is a bottom plan view of the surgical frame;

FIG. 5 is a cross-sectional view of a connection between the first and second frame portions as seen along line V—V of FIG. 3;

FIG. 6 is a partial elevational view of the surgical frame as seen along line VI—VI of FIG. 3; and, FIG. 7 is a partial elevational view of the surgical frame as seen along line VII—VII of FIG. 3.

DETAILED DESCRIPTION OF THE PREFERRED EMBODIMENT

Figure 1:
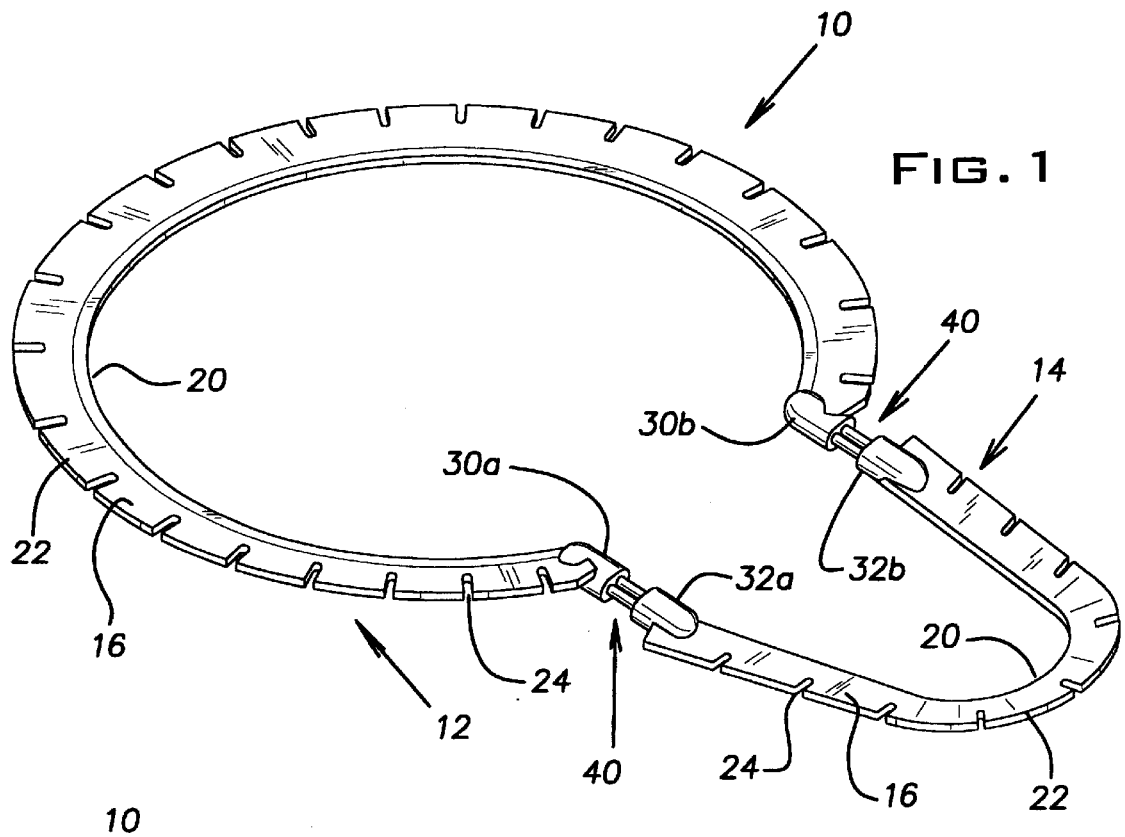
FIG. 1 is a perspective view of a surgical frame according to the present invention in a first configuration wherein first and second portions of the frame are in alignment with one another.

It should be noted that in the detailed description that follows, identical components have the same reference numeral, regardless of whether they are shown in different embodiments of the present invention. It should also be noted that in order to clearly and concisely disclose the present invention, the drawings may not necessarily be to scale and certain features of the invention may be shown in somewhat schematic form. It should be further noted that the peripheral shape (i.e., circular and V-shaped) of the illustrated frame portions is exemplary of two common frame portion shapes. However, the present invention is not to be limited to a surgical frame with frame portions having the illustrated shapes. Rather, several frame portion shapes are known in the art and are considered interchangeable with those illustrated herein.

With reference to the drawing figures, a surgical frame 10 according to the present invention is illustrated. The surgical frame includes a first portion 12 and a second portion 14. The first frame portion 12 is generally arcuate or circular, while the second frame portion 14 is somewhat V-shaped, as illustrated. The following description of the structural features of the surgical frame 10 is generic insofar as the description is equally applicable to the first and second frame portions.

Figure 2:
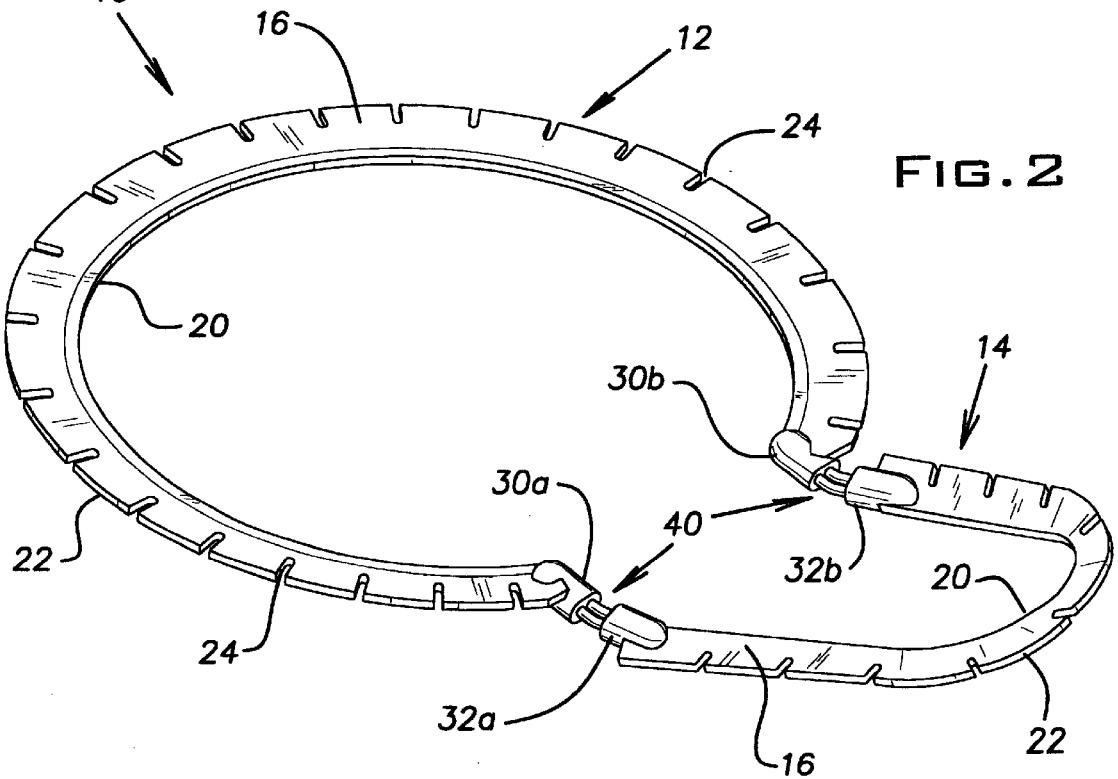
FIG. 2 is a perspective view of a surgical frame in a second configuration wherein the first and second frame portions are at an angle relative to one another.

The surgical frame 10 has an upper surface 16 (FIGS. 1–3) and a lower surface 18 (FIG. 4). The upper surface 16 is substantially planar, and angles from a relatively lower, inner edge 20 to a relatively higher, outer edge 22. At the outer edge 22 a plurality of regularly spaced notches 24 are formed in the surgical frame 10 to facilitate attachment of surgical stays (not shown) thereto. It is noted that surgical stays are well known in the art and do not form part of the present invention. Accordingly, surgical stays are not illustrated and will not be further discussed hereinafter. If further information regarding surgical stays is desired, reference should be made to U.S. Pat. Nos. 5,785,649; 5,769,783;

5,514,076; 4,610,243; 4,430,991; and U.S. Pat. No. Re. 32,021, the disclosures of which are expressly incorporated herein by reference.

The lower surface 18 of the surgical frame 10 has an inner, raised rim 26 and an outer peripheral flange 28. The flange 28 slopes downwardly and outwardly away from a base of the raised inner rim 26, and generally matches the angle or slope of the frame upper surface 16. The notches 24 extend through the lower surface 18 at the outer flange 28, as illustrated. As such, the radially outer portion of the frame 10 is angled relative to the axis of the frame and has a generally constant thickness. The radially inner portion of the frame 10 has a thickness that is increased relative to the outer portion or flange 28.

In using the surgical frame, the raised inner rim 26 on the lower frame surface 18 is placed in contact with a body surface surrounding the surgical field. The rim 26 serves to maintain the outer flange 28 elevated relative to the body surface. Spacing or maintaining the flange 28 above the surface of the body facilitates insertion and retention of the surgical stays in the notches 24. The shape of the surgical frame 10 also helps to resist compressive forces exerted by the surgical stays, and generally provides a stable, self-retaining structure, so long as the stays are inserted into diametrically opposed pairs of frame notches.

With continuing reference to the drawing figures, the first and second frame portions 12, 14 each include first and second ends 30a, 30b; 32a, 32b. The first end 30a of the first frame portion 12 faces the first end 32a of the second frame portion 14. The second end 30b of the first frame portion 12 faces the second end 32b of the second frame portion 14. Each of the ends 30a, 30b; 32a, 32b includes a relatively enlarged socket member 36 that receives a connector 40 for securing the first and second frame portions 12, 14 together.

More specifically, the connector 40 is preferably formed from a malleable material and is inserted into and adhesively secured to the first and second frame portions 12, 14. Although adhesive attachment of the connector 40 to the frame portions 12, 14 is preferred due to labor, cost, and manufacturing flexibility considerations, the connector 40 may be insert-molded into the first and second frame portions 12, 14.

The connector 40 is preferably a solid core wire material 42 having a vinyl or plastic outer coating 44. Preferably, the each connector 40 has a first end 46 adhesively secured to the first frame portion 12 and a second, opposite end 48 adhesively secured to the second frame portion 14. More preferably, and as illustrated, first and second pairs of such connectors 40 are used to secure the first and second frame portions 12, 14 to one another. A first pair of connectors connects the first ends 30a, 32a of the first and second frame portions 12, 14 to one another. A second pair of connectors connects the second ends 30b, 32b of the first and second frame portions 12, 14 to one another.

Provision of a pair of connectors 40 on each side resists twisting of the first and second frame portions. Two such connectors on each side is also preferred because it permits the desired connector strength and stability while permitting connectors of a desired cross-sectional size. Naturally, more or less than two connectors may be used without diverging from the scope of the present invention.

Reorientation of the frame portions 12, 14 relative to one another is facilitated with a surgical frame 10 constructed in accordance with the present invention. Since the connector 40 is malleable, the first frame portion 12 is simply bent or pivoted relative to the second frame portion 14. Such bending or pivoting will reconfigure the surgical frame 10 from a first configuration (FIG. 1) to a second configuration (FIG. 2), for example.

In accordance with the present invention, desired orientation of the frame portions 12, 14 does not require loosening, tightening, or otherwise turning or manipulating connectors or mechanical fixtures that interconnect the first and second frame portions 12, 14. Rather, with the present invention, the surgical frame 10 may simply be placed on the body such that the surgical field is surrounded by the first and/or second frame portions 12, 14, as desired. Thereafter, the first and/or second frame portions 12, 14 are pushed downwardly toward the body, thereby bending the connector 40 and urging the surgical frame 10 into better conformance with the contour of the patient's body. As such, the surgical frame 10 is in a convenient position for attachment of the surgical stays. Accordingly, the present invention facilitates easy and rapid positioning of the surgical frame by a surgeon.

The preferred embodiment of the present invention is described and illustrated herein. However, it is considered apparent that numerous modifications, substitutions of parts, and additions may be made without departing from the scope and spirit of the present invention as embodied by the claims appended hereto. For example, while the connector preferably extends only between the first and second frame portions, it is considered apparent that the wire material may form a loop that is integrally molded into the first and second portions. Such a loop may be molded into the rim of the frame portions. Moreover, while a plastic coated wire is preferred as the connector, it is also considered apparent that numerous other connectors may be employed interchangeably so long as the function of the connector discussed hereinbefore is preserved. For example, instead of having individual plastic-coated wires, it is contemplated that a plurality of wires may be embedded or surrounded in a flexible membrane or sheath. Further, it is contemplated that the wires be replaced by a different malleable member, including one that may preclude bending in a predetermined direction. Such a different malleable member may be a metal ribbon that is bendable in one direction but not bendable in a second, perpendicular direction. Accordingly, the present invention is not limited to the structure specifically described and illustrated hereinbefore, but rather covers and includes all that is defined by the following claims.

What is claimed is:

1. A retractor frame formed from a substantially rigid material, said frame comprising a first frame portion and a second frame portion which cooperate to define a support adapted to surround a surgical field and to releasably receive a plurality of surgical stays for temporary retraction of tissue during a surgical procedure, the improvement comprising:

means for permanently securing the first frame portion to the second frame portion, said securing means being deformable to permit the first and second portions to be moved relative to one another.

2. A retractor frame according to claim 1, wherein said securing means comprises a connector that extends between said first and second frame portions, said connector being permanently attached to each of said first and second portions.

3. A retractor frame according to claim 1, wherein said securing means comprises a pair of connectors, each of said pair of connectors extending between said first and second frame portions and being permanently attached to each of said first and second frame portions.

4. A retractor frame according to claim 1, wherein deformation of said securing means is reversible.

5. A retractor frame according to claim 2, wherein said first and second frame portions are made from a molded material and said connector is made from a malleable material, said securing means having a first end affixed to said first frame portion and a second end affixed to said second frame portion.

6. A retractor frame according to claim 3, wherein said first and second frame portions are made from a molded material and said pair of connectors are made from a malleable material, each of said pair of connectors having a first end affixed to said first frame portion and a second end affixed to said second frame portion.

7. A retractor frame according to claim 4, wherein said securing means comprises a connector that extends between said first and second frame portions, said connector being permanently attached to each of said first and second frame portions.

8. A retractor frame according to claim 4, wherein said securing means comprises a pair of connectors, each of said pair of connectors extending between said first and second frame portions and being permanently attached to each of said first and second frame portions.

9. A retractor frame according to claim 7, wherein said first and second frame portions are made from a molded material and said connector is formed made a malleable material, said connector having a first end affixed to said first frame portion and a second end affixed to said second frame portion.

10. A retractor frame according to claim 8, wherein said first and second frame portions are made from a molded material and said pair of connectors are made from a malleable material, each of pair of connectors having a first end affixed to said first frame portion and a second end affixed to said second frame portion.

11. A retractor frame according to claim 9, wherein said connector comprises at least one wire.

12. A retractor frame according to claim 11, wherein said at least one wire is adhesively attached to said first and second frame portions.

13. A retractor frame according to claim 12, wherein said at least one wire is surrounded by a plastic sheath.

14. A retractor frame according to claim 10, wherein each of said pair of connectors comprise at least one wire.

15. A retractor frame according to claim 14, wherein said at least one wire is adhesively attached to said first and second frame portions.

16. A retractor frame according to claim 15, wherein said at least one wire is surrounded by a plastic sheath.

\* \* \* \* \*